United States Patent [19]

Israel

[11] Patent Number: 4,589,867
[45] Date of Patent: May 20, 1986

[54] EXPONENTIAL MIXING AND DELIVERY SYSTEM

[76] Inventor: Michael B. Israel, 29 Gann Rd., East Hampton, N.Y. 11937

[21] Appl. No.: 671,965

[22] Filed: Nov. 16, 1984

[51] Int. Cl.⁴ ............................................. A61M 5/00
[52] U.S. Cl. ..................................... 604/85; 604/410
[58] Field of Search .............................. 604/56, 82–92, 604/408–410, 416

[56] References Cited

U.S. PATENT DOCUMENTS

| | | | |
|---|---|---|---|
| 1,373,018 | 3/1921 | Palmer | 604/85 X |
| 3,204,633 | 9/1965 | Hofstra | 604/245 |
| 3,993,066 | 11/1976 | Virag | 604/86 X |
| 4,250,879 | 2/1981 | Muetterties et al. | 604/83 X |
| 4,396,383 | 8/1983 | Hart | 604/82 X |
| 4,467,588 | 8/1984 | Carveth | 604/92 X |
| 4,484,920 | 11/1984 | Kaufman et al. | 604/416 |

*Primary Examiner*—Dalton L. Truluck
*Attorney, Agent, or Firm*—Edith T. Grill

[57] ABSTRACT

A nonvented gravity fed exponential mixing and delivery system and apparatus for the administration of a drug in a precalculated manner to give constant therapeutic blood plasma levels in the recipient, (patient), which provides an inexpensive, quick and simple exponential mixing procedure to deliver an infusion containing exponentially decreasing concentrations of a drug.

13 Claims, 2 Drawing Figures

EXPONENTIAL MIXING AND DELIVERY SYSTEM

BACKGROUND AND PRIOR ART

The present invention relates to a novel nonvented gravity fed exponential mixing and delivery system and apparatus useful for the administration of a drug in a precalculated manner to give constant therapeutic blood plasma levels in the patient.

The prior art discloses gravity fed intravenous (IV) administration systems for controlling the quantity of a single fluid to be delivered to the patient and/or to provide a controlled rate of flow thereof, as shown in U.S. Pat. Nos. 2,827,081, No. 2,853,069, No. 4,000,738, and No. 4,136,693. However, none of aforesaid systems include, nor make provision for, the mixing of two liquids generally or exponentially.

The prior art also discloses the insertion of mixing devices into an IV system for mixing two liquids or a solid and a liquid, to form a single solution of equal concentration during the total infusion period, as disclosed in U.S. Pat. No. 3,670,728 wherein two different liquids are packaged in a dual chamber flask separated by a septum capable of being upset to enable mixing of the two liquids, assisted by inletting air at the bottom of the flask and initiated by a pumping device for hand operation. U.S. Pat. No. 4,392,850 discloses an in-line transfer container containing a solid material to be intermixed in an IV solution, and serving as a mixing container, disposed below the IV solution container and provided with pierceable diaphragms at opposing ends to provide a fluid passageway for the incoming IV solution into the mixing container, wherein the flexible end wall thereof, is pumped to assist in the intermixing of the IV solution with the material in the mixing chamber, and subsequently piercing the opposing diaphragm to permit the fluid mixture to flow through the IV tubing to the patient. The use of this device involves multiple steps, requiring human intervention, and an excessive amount of time which may be life threatening in an emergency situation. U.S. Pat. No. 4,410,321 discloses a closed drug delivery system for separately storing and selectively mixing two components such as a drug and diluent under sterile conditions, comprising a compressible chamber containing a sterile liquid, a drug vial and a pierceable access means therebetween to create a pathway for the drug to flow into the compressible chamber which is positioned by hand manipulation to facilitate mixing of the drug and the liquid into a solution of uniform concentration for administration to the patient. However, none of aforesaid mixing systems effect exponential mixing nor are they gravity fed.

U.S. Pat. No. 4,424,056 discloses a parenteral administration system of delivering a fluid through a primary path, and a mixture of fluid and medicinal agent through a parallel path wherein the fluid passes through a formulation chamber containing an agent which dissolves in said fluid, and flows into the primary path for delivery to the patient at a controlled rate. The mixing that occurs in the formulation chamber is not exponential mixing.

None of aforesaid patents relate to the particular problems associated with the administration of certain drugs which require a constant plasma drug concentration, small variations thereof being either therapeutically ineffective or toxic. In either case, the results may be serious. This is particularly applicable in the intravenous administration of antiarrhythmic drugs such as lidocaine and other drugs that require a constant plasma drug concentration. Prior art methods used a loading dose and a maintenance infusion at a constant rate. This has been found to be suboptimal due to the production of wide variations in plasma drug concentrations early in therapy. Another prior art method used a series of precisely timed infusion rate changes, which merely minimized said variability and had the additional disadvantage of requiring human intervention at said timed intervals, which detracts from the ability to devote maximum attention to critical patients.

The best method heretofore utilized is the administration of an initial loading dose and an exponentially decreasing infusion rate obtained by approximation using mechanical constant rate infusion pumps and stepped decreases in the delivery rate. This method has the disadvantage of requiring frequent human intervention which is undesirable in a clinical setting.

An improvement on the above exponential infusion rate method utilizing a constant flow rate, is disclosed in *Annals of Internal Medicine*, 1984, Vol. 100, pp. 25-28, wherein a diluting solution of the drug, e.g. lidocaine, is mechanically pumped from a vented IV set into the base of a 20 ml multiple dose vial containing 1% lidocaine at a rate of 1 ml/min, said entering solution displacing solution at an equal rate from a needle inserted at the base of said vial. The resulting infusion concentration which decreases exponentially, is delivered to the patient. This apparatus has the disadvantage of requiring expensive equipment as well as cumbersome, such as a pump, which requires human intervention to start and stop said pump. There is a possibility of mechanical malfunction of the pump which would interfere with the drug infusion into the patient and its concomitant adverse effects such as insufficient drug therapy or toxic side effects due to increased drug infusion. The use of vented equipment is open to contamination from the air and a potential break in the sterility of the drug infusion.

None of the above cited art discloses a gravity fed, non-vented exponential mixing and delivery system and apparatus for the administration of a drug in a precalculated manner to give constant therapeutic blood plasma levels in the recipient.

SUMMARY OF THE INVENTION

It has now been found that the administration of a therapeutic agent in a precalculated manner to give constant therapeutic blood plasma levels in the patient, can be obtained quickly, efficiently, under sterile conditions, and in the absence of human intervention during the administration of the agent by using present novel non-vented gravity fed exponential mixing and delivery system which comprises the exponential mixing of a dilute solution of the agent which flows by gravity from an upper sealed deformable container, through a common access means, into a lower nondeformable mixing chamber of reduced size, filled to capacity with a more concentrated solution of said drug, said mixing container being provided with a vertical inlet conduit means and a vertical outlet conduit means at opposing ends, each conduit means extending into said mixing container at a height to provide a sufficient height differential to induce exponential mixing of the solutions, to effect an exponentially decreasing concentration of said drug during a constant infusion rate, flowing through said outlet conduit and into a conventional non-vented administration apparatus which may include a minidrip chamber to regulate the flow rate, and IV tubing provided with a flow rate control valve, and a sealed side-arm.

The non-vented gravity fed exponential mixing and delivery system, and apparatus generally comprises a sealed deformable upper container containing a drug-free solvent or diluent such as a dextrose solution, or a dilute solution of the drug, vertically aligned and contiguous with a nondeformable lower mixing container of reduced size filled to capacity with a more concentrated solution of said drug, means in the upper container for initiating or activating the gravity flow of the dilute solution from the upper container into the lower mixing container, a communication means between the upper and lower containers, said lower mixing container being provided with an inlet conduit means and an outlet conduit means on opposing ends, the height differential between said conduit means operable to effect exponential mixing, a minidrip chamber connected to said outlet conduit means to receive and regulate the flow of the exponentially decreasing concentration of said drug in the infusion per unit of time at a constant flow rate, to the patient by means of intravenous (IV) tubing provided with a control valve and sealed side-arm. Optionally, the lower end of the outlet conduit means is provided with a pierceable closure means adapted to connect to a nonvented administration set which may include a minidrip chamber, and IV tubing provided with a flow control valve and sealed side-arm.

The apparatus for implementing present novel gravity fed exponential mixing and delivery system is preferably in the form of a sealed, disposable prepackaged kit comprising a deformable upper container in folded condition filled with a dilute solution of a drug or diluent vertically aligned and contiguous with a nondeformable lower mixing container of reduced size filled to capacity with a more concentrated solution of said drug, said upper container being provided with an internal removable closure means integral with and depending from the top thereof, which is inserted into a vertical inlet conduit means extending downwardly from the top wall of the lower container, at the common access means between the upper and lower containers, said lower mixing container being additionally provided with a vertical outlet conduit means extending upwardly from the bottom wall, the height differential between said conduit means operable to effect exponential mixing in said mixing container, a pierceable closure means at the lower end of said outlet conduit means adapted to connect to conventional non-vented administration sets; or alternatively, said outlet conduit means is connected directly to a minidrip chamber, and IV tubing provided with a flow rate control valve, and a sealed side-arm, as part of the package.

DESCRIPTION OF THE DRAWINGS

The following drawings more specifically describe present invention, wherein.

Figure 1:
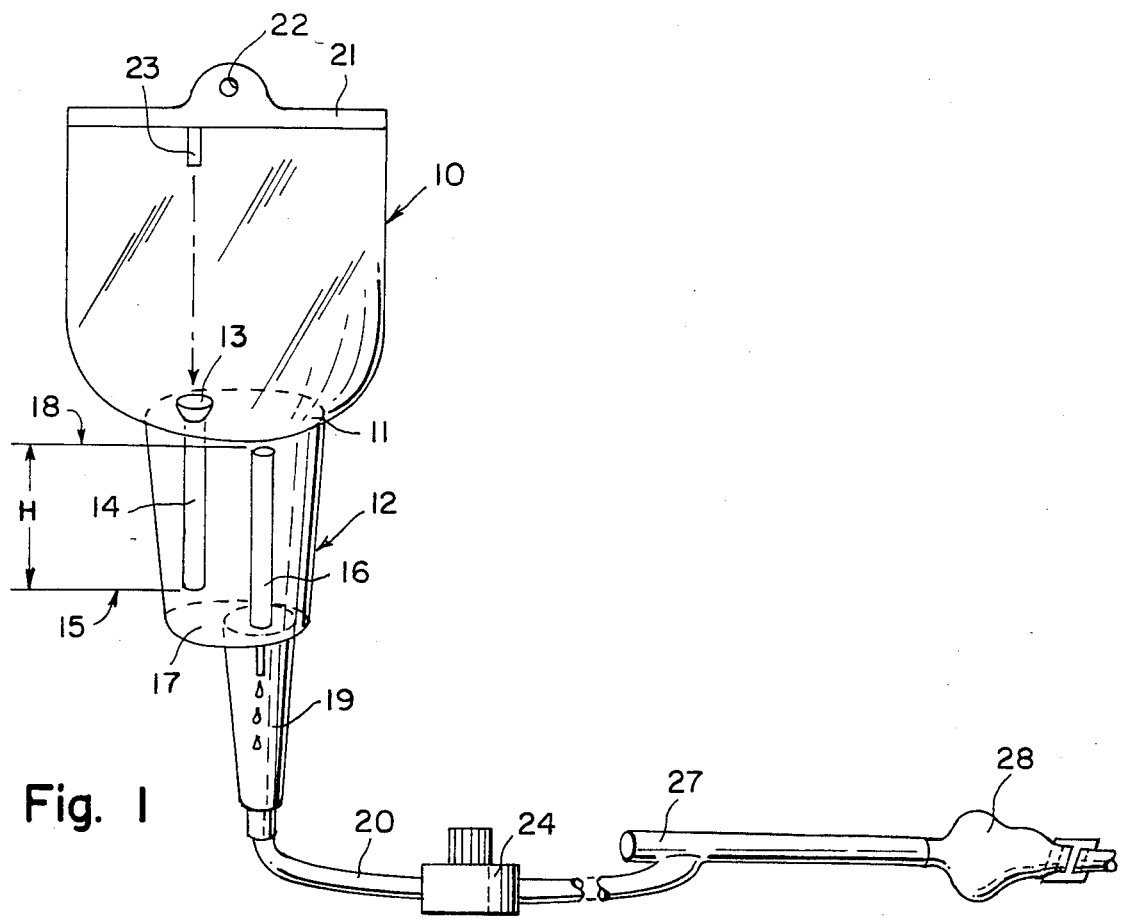
FIG. 1 is an elevational view of the exponential mixing and delivery system embodying the principles of this invention in operation.

In said drawings, the gravity fed exponential mixing and delivery system comprises a sealed deformable upper container 10, containing a sterile diluting solution of a therapeutic agent or a solvent, sealed to the top wall 11, of a nondeformable lower mixing container 12, of reduced size, filled to capacity with a more concentrated sterile solution of said agent, a common access means such as opening 13, in top wall 11, of lower container 12, to permit the gravity flow of liquid from the upper container 10, into lower container 12, through inlet tube 14, depending from top wall 11, and in communication with opening 13, said inlet tube extending downwardly into mixing container 12, to a height 15, such that the height differential H, between inlet tube 14, and outlet tube 16, integral with bottom wall 17, and extending upwardly to a height 18, is operable to effect exponential mixing in container 12. Said mixture of exponentially decreasing concentrations of the drug flows via outlet tube 16, into a minidrip chamber 19, at a regulated flow rate and through IV tubing 20, to the patient by opening a valve 24 for controlling the flow rate. The flow rate is regulated by the diameter of the flexible IV tubing. Exponential mixing of solutions will not occur until closure plug 23 is removed, and the flow of solution through outlet tube 16 commences. This ensures no mixing until this apparatus is connected to the patient and the infusion commences by opening flow rate valve 24.

Mixing container 12 is ductile but nondeformable and preferably made of clear plastic.

Deformable container 10 may be in the form of a flexible IV bag sealed at the top 21, and provided with a grommet 22, or with other suitable suspension means within sealed top 21, by which container 10, may be suspended from a bracket or other suitable support means (not shown).

Figure 2:
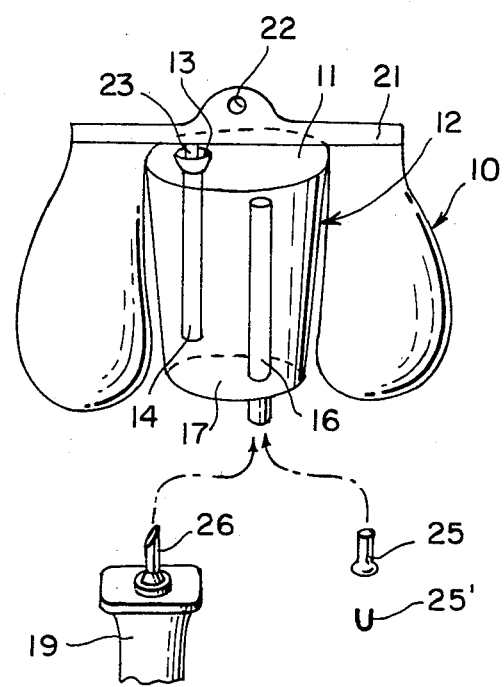
FIG. 2 is an elevational view of the exponential mixing and delivery apparatus embodying the principle of the invention prior to use in a prepackaged kit.

Container 10 is further provided with an internal removable closure means 23, such as a plug integral with, and depending from sealed top 21, which frictionally fits into inlet tube 14, at access opening 13, when in folded condition prior to use (FIG. 2). Removal of closure means, plug 23, from tube 14, can be readily obtained by simply hanging which simultaneously unfolds flexible container 10, onto a suitable suspending support, by means of grommet 22. The removal of plug 23, from inlet tube 14, initiates the gravity flow of liquid from container 10, into container 12, through common access opening 13; and exponential mixing commences in mixing container 12 upon opening outlet tube 16 to the flow of solution into the minidrip chamber 19, of the IV administration set.

Plug 23 is inserted in tube 14, to guarantee no flow prior to removal of mixing chamber from package and hanging of the flexible bag 10.

The prepackaged kit may comprise the dual containers, i.e. the flexible container folded over onto both sides of the nondeformable mixing container 12, provided with an airtight pierceable seal which may be in the form of a plug 25, or a plastic diaphragm 25′, inserted into outlet tube 16, adaptable for the insertion of conventional non-vented administration sets by means of a hollow spike 26, leading into a minidrip chamber 19, connected to IV tubing 20, with sealed side-arm 27. Alternatively, the kit may also include the administration set, i.e. the plug 25 or diaphragm 25′ may be omitted, and the outlet tube 16 may be directly connected to the minidrip chamber 19, which is connected to IV tubing 20, provided with flow control valve 24, side-arm 27, and leak proof seal 28, to insure no flow prior to use, i.e. before connection to the infusion needle in the patient.

The packaged kit is sealed to prevent air from entering, thereby ensuring sterility prior to use as well as during use.

The ratio of volumes of the upper container to the lower container is a minimum of about 10:1 in order to effect exponential mixing, the amount of solution in flexible container 10, being a resultant of the volume of solution in nondeformable container 12, which is filled to capacity.

For example, flexible bag 10 is filled with 1 liter of an aqueous solution containing 5% dextrose and 2 grams lidocaine, and the nondeformable container 12 is filled to capacity with 20 cc of dextrose water containing 1% lidocaine (200 mg lidocaine). The solution from bag 10 flows by gravity into container 12 through inlet tube 14 which is ⅛" diameter 27 gauge, wherein the solutions are exponentially mixed, and flows out of container 14 through outlet tube 16 which is 1½" diameter 22 gauge, into minidrip chamber 19, and is delivered to standard width IV tubing 20 at a rate of 1 drop/sec which is equal to 1 cc/min. A sufficient height differential of inlet tube 14 and outlet tube 16 ensures exponential mixing according to the equation:

$$R_t = Q[C_d + (C_i - C_d)e^{-\frac{Q}{V}t}] \quad \quad 1$$

wherein $R_t$ = delivery rate gradient
$C_i$ = initial drug concentration of volume V in mixing chamber
$C_d$ = drug concentration of the diluting solution in flexible bag
Q = constant rate of delivery of diluent and removal of solution from the mixing chamber
t = time
e = exponential function According to this equation, this should deliver an infusion with a concentration of therapeutic agent which decreases exponentially from an initial rate of 10 mg/min to 2 mg/min with a half-life of 13.86 minutes.

While equation 1 is specific to the exponentially decreasing delivery of lidocaine from container 12 as induced by a solution from container 10 which is of lower concentration than the initial concentration, the invention can also be used to address the problem of an exponentially decreasing delivery rate of a solution from container 12 at a constant rate, as induced by a pure solvent from container 10, equation 1 then being altered as detailed by C. J. Morris and P. Morris in *Separation Methods in Biochemistry*, 2nd edition, 1976; 103–4.

This invention is also applicable to other agents which are not governed by the same pharmacokinetic approach as lidocaine, which would then follow the equations to obtain an instantaneous plasma drug concentration and to maintain it at a constant value, as derived by D. P. Vaughan and G. T. Tucker, in the *European Journal of Clinical Pharmacology*, 1976, Vol. 10, 433–40.

The height differential of outlet tube and inlet tube is effected by the volume and thus the design of the container itself. Generally, for containers of small capacity, such as discussed above, as long as the end of each tube is positioned at the extreme opposite end to the tubes' point of entry without restricting flow, the criteria of the design is met. To be more specific, the laws of diffusion/mass transport are governed by the rate of mass transfer.

The rate of mass transfer is given by Fick's first law as:

$$\tilde{I}_A = -D_{AB}\frac{d\tilde{\rho}A}{dy} \quad \quad 2$$

for ordinary molecular diffusion in the y direction at constant molal density. The quantity $\tilde{I}_A$ is the flux of the constituent A, measured in lb moles/(hr)(sq ft), and $d\tilde{\rho}A/dy$ is the gradient of the concentration, in lb moles/cu ft (ft), which acts as a driving force. The symbol $D_{AB}$ represents the diffusivity, or coefficient of diffusion, for a binary mixture of species A and B. $D_{AB}$ is a function of composition.

This novel and useful invention provides an exponential mixing and delivery system and apparatus for the administration of a therapeutic agent to yield rapidly attained and maintained constant therapeutic plasma levels, by simply opening a sterile prepackaged kit, hanging it on a suitable support, connecting the outlet tube to the minidrip chamber of an IV administration kit, which leads into the patient, administering one bolus injection of 1 mg/kg body weight, through sidearm 27 at the start of said infusion or shortly thereafter. The infusion starts immediately and requires no other human intervention until the contents are exhausted. The exponentially decreasing amount of therapeutic agent insures a constant concentration of therapeutic agent in the blood plasma, thereby avoiding toxicity due to an overdose, or ineffectual drug therapy due to an underdose. This is of particular importance in emergency or critical clinical situations such as in patients with cardiac failure or with concurrent decreased hepatic or renal function.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

I claim:

1. A non-vented, gravity fed exponential mixing and delivery system for the administration of a therapeutic agent in a precalculated manner to give constant therapeutic blood plasma levels in the recipient which comprises an upper sealed deformable container for containing a dilute solution of a therapeutic agent, provided with a hanging means, a removable internal closure means within said upper container for initiating the gravity flow of the dilute solution into a lower mixing container, a lower nondeformable mixing container integral with the upper container for containing a concentrated solution of said agent, a common access means between the upper and lower containers for the flow of solution from the upper container into a vertical inlet conduit means extending into the lower mixing container, a vertical outlet conduit means extending upwardly into the lower mixing container to provide a height differential between inlet and outlet conduit means for the exponential mixing of the dilute and concentrated solutions, said vertical outlet tube also extending downwardly into a minidrip chamber for the flow of exponentially dicreasing concentrations of said therapeutic agent at a constant infusion rate and at a regulated flow rate to the patient.

2. The system according to claim 1, wherein the removal of the closure means from inlet conduit means is obtained by hanging and simultaneously unfolding the deformable container.

3. The system according to claim 1, wherein the ratio of volumes of the upper container to the lower container is a minimum of about 10:1.

4. The system according to claim 1, wherein the height differential of inlet and outlet conduit means, sufficient to effect exponential mixing for containers of small capacity, is obtained by extending the end of each tube to the extreme opposite end of the conduit means' point of entry without restricting flow.

5. A non-vented gravity fed exponential mixing and delivery apparatus comprising a sealed deformable upper container provided with a hanging means and containing a dilute solution of the drug, vertically aligned and contiguous with a nondeformable lower mixing container of reduced size filled to capacity with a more concentrated solution of said drug, a communication means between the upper and lower containers, said lower mixing container being provided with an inlet conduit means and an outlet conduit means on opposing ends, the height differential between said conduit means operable to effect exponential mixing, said upper container provided with an internal removable closure means integral with and depending from the top thereof which frictionally fits into the inlet conduit means of the lower container as the control means for initiating or activating the gravity flow of the dilute solution from the upper container into the lower mixing container, a minidrip chamber connected to said outlet conduit means to receive and regulate the flow of the exponentially decreasing concentration of said drug in the infusion per unit of time, at a constant flow rate, to the patient, by means of intravenous (IV) tubing provided with a control valve and sealed side-arm.

6. The apparatus according to claim 5, wherein said deformable container is in the form of a flexible bag sealed at the top and provided with a suspension means within said sealed top for hanging said bag onto a support means.

7. The apparatus of claim 5, wherein the ends of the inlet and outlet conduit means within the lower container extend to the extreme opposite end of each conduit means' point of entry without restricting flow to effect exponential mixing in containers of small capacity.

8. The apparatus according to claim 5, wherein the deformable upper container contains a drug-free solvent or diluent.

9. A sealed, disposable prepackaged kit comprising a deformable upper container in folded condition filled with a dilute solution of a drug, vertically aligned and contiguous with a nondeformable lower mixing container of reduced size filled to capacity with a more concentrated solution of said drug, said upper container being provided with an internal removable closure means integral with and depending from the top thereof, which is inserted into a vertical inlet conduit means extending downwardly from the top wall of the lower container, at the common access means between the upper and lower containers, said lower mixing container being additionally provided with a vertical outlet conduit means extending upwardly from the bottom wall, the height differential between said conduit means operable to effect exponential mixing in said mixing container, a pierceable closure means at the lower end of said outlet conduit means adapted to connect to conventional nonvented administration sets.

10. The prepackaged kit according to claim 9, wherein said outlet conduit means is connected directly to a minidrip chamber, IV tubing provided with a flow rate control valve, sealed side-arm, and terminating in a leak proof seal.

11. The kit according to claims 9 or 10, wherein said deformable bag is in the form of a flexible bag sealed at the top and provided with a grommet within said sealed top for suspending said bag from a support means.

12. The kit according to claim 9 wherein the ends of the inlet and outlet conduit means within the lower container extend to the extreme opposite end of each conduit means' point of entry without restricting flow, to effect exponential mixing in containers of small capacity.

13. The apparatus according to claim 9, wherein the deformable upper container is filled with a drug-free solvent.

* * * * *